(12) United States Patent
Birk et al.

(10) Patent No.: US 7,401,377 B2
(45) Date of Patent: Jul. 22, 2008

(54) BATTERY-OPERATED TOOTHBRUSH AND RELATED METHODS

(75) Inventors: Andreas Birk, Bad Homburg (DE); Soren Wasow, Mainz (DE)

(73) Assignee: Braun GmbH, Kronberg (DE)

( * ) Notice: Subject to any disclaimer, the term of this patent is extended or adjusted under 35 U.S.C. 154(b) by 0 days.

(21) Appl. No.: 11/292,401

(22) Filed: Nov. 30, 2005

(65) Prior Publication Data
US 2006/0112505 A1 Jun. 1, 2006

(30) Foreign Application Priority Data
Nov. 30, 2004 (DE) .................. 10 2004 057 566

(51) Int. Cl.
*A61C 3/00* (2006.01)
*A45B 9/04* (2006.01)
(52) U.S. Cl. .................. 15/167.1; 15/184; 15/22.1; 15/24; 15/29
(58) Field of Classification Search .................. None
See application file for complete search history.

(56) References Cited

U.S. PATENT DOCUMENTS

| 4,413,199 | A | 11/1983 | Fischer |
| 7,240,390 | B2 | 7/2007 | Pfenniger et al. |
| 2003/0154567 | A1 | 8/2003 | Drossler et al. |
| 2004/0007244 | A1 | 1/2004 | Harms |
| 2004/0060138 | A1 * | 4/2004 | Pfenniger et al. ............ 15/22.1 |
| 2004/0154113 | A1 | 8/2004 | Drossler et al. |
| 2005/0271997 | A1 * | 12/2005 | Mikami et al. ................ 433/29 |

FOREIGN PATENT DOCUMENTS

| DE | 2904327 A1 | 8/1980 |
| DE | 10061327 A1 | 6/2002 |
| DE | 10206493 A1 | 8/2003 |
| DE | 10245086 A1 | 4/2004 |
| WO | WO 01/82825 | 11/2001 |

OTHER PUBLICATIONS

European Search Report for European Application No. EP 05024996 dated Mar. 8, 2006 (2pp.).

* cited by examiner

*Primary Examiner*—David A Redding
(74) *Attorney, Agent, or Firm*—Fish & Richardson P.C.

(57) ABSTRACT

A battery-operated toothbrush includes a drive unit, a housing defining an accommodation chamber configured to receive the drive unit, and a thermoplastic elastomer seal disposed on an outer surface of the housing. The housing includes a front end configured to receive a toothbrush head, an open end, opposite the front end, that provides access to the accommodation chamber, and a pass-through aperture, which extends from an outer surface of the housing to the accommodation chamber. The drive unit includes an engagement element configured to engage the pass-through aperture to retain the drive unit in the accommodation chamber. The thermoplastic elastomer seal extends into the pass-through aperture. A potion of the thermoplastic elastomer seal is elastically displaced by the engagement element when the engagement element engages the aperture.

15 Claims, 1 Drawing Sheet

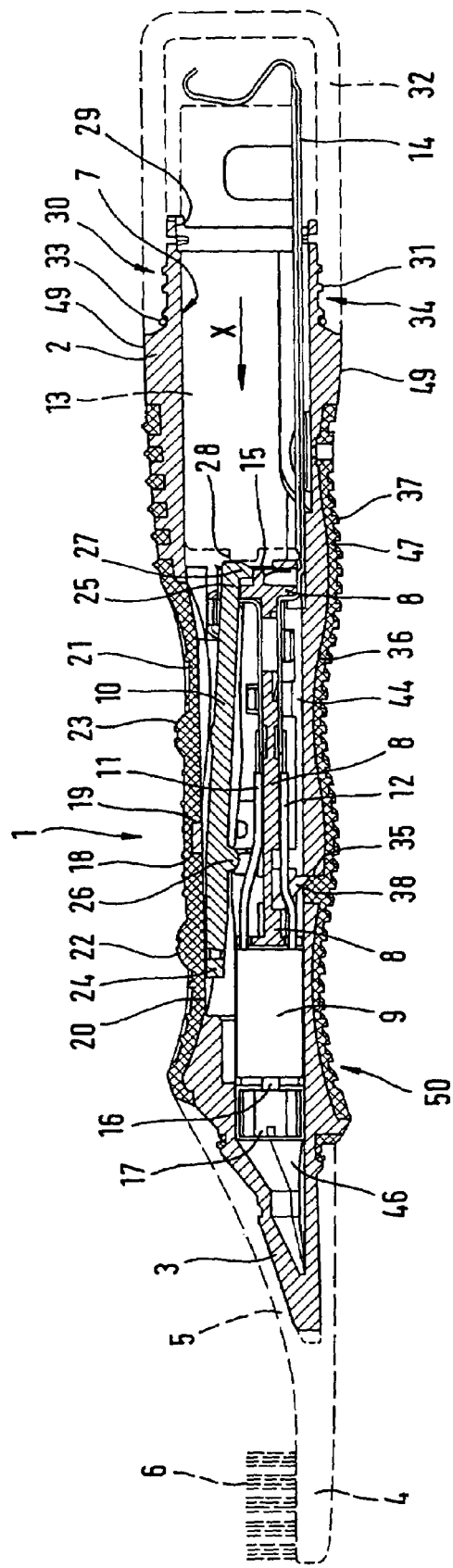
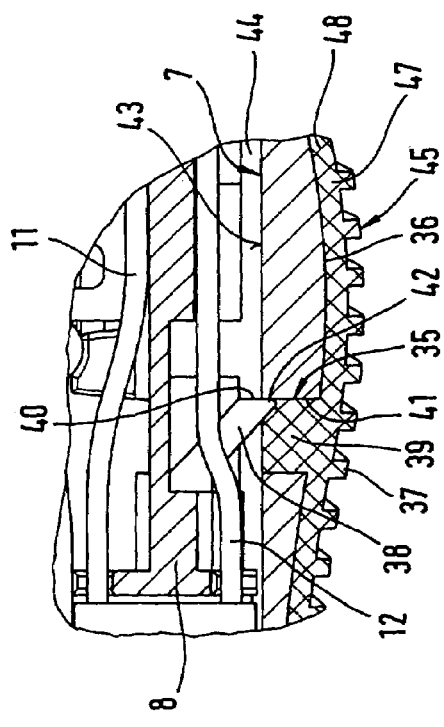
Fig. 1
Fig. 2

BATTERY-OPERATED TOOTHBRUSH AND RELATED METHODS

CROSS-REFERENCE TO RELATED APPLICATIONS

This application claims priority under 35 U.S.C. § 119(a) to German Patent Application No. 10 2004 057 566.5, filed on Nov. 30, 2004, which is incorporated herein by reference in its entirety.

TECHNICAL FIELD

The invention relates to battery-operated toothbrushes and related methods.

BACKGROUND

Battery-operated toothbrushes are known in the art. For example, German Patent No. DE 102 45 086 A1 describes a battery-operated toothbrush including a housing section that is injection molded around a drive unit, or essential parts of the drive unit, thereby fixing the drive unit in place in the housing section. If temperature-sensitive components are used in the drive unit, the thermal effect of injection molding the housing can damage or even destroy the drive unit components.

Moreover, a battery-operated toothbrush that is marketed by the assignee (Braun GmbH) itself is known and is commercially available under the name "Braun Oral-B Cross Action Power." This battery-operated toothbrush includes a tubular housing, to which a toothbrush head is attached at one end. The other end includes, an opening through which the drive unit, which is attached to a preassembled retaining element (e.g., by clipping) is inserted into the tubular housing section during assembly. Two engaging means are located on the retaining element, which clip into place when the drive unit together with the retaining element is inserted into two pass-through openings formed on the housing part.

The pass-through openings are formed near the opening inside a screw thread, which is disposed on an outer surface of the housing section and adjacent the opening. The screw thread of the housing connects in a torque-proof manner with a corresponding thread of a sealing cap. A replaceable battery, which is electrically connected with the drive unit via contact terminals, is also coupled to the retaining element and in the housing section. When the drive unit is assembled, part of the battery and part of the retaining element, project out of the opening, while the front parts of the drive unit and the retaining element are accommodated in the bore of the housing section.

The tubular housing section is made from plastic and is formed in a tool in an injection molding process. In order to prevent moisture from penetrating the interior of the drive unit via the pass-through openings, the pass-through openings are formed in the thread section, which is enclosed and made waterproof by a sealing cap. An O-ring placed on the thread provides a substantially watertight seal between the sealing cap and the housing section. However, according to this arrangement, the pass-through openings must be locally fixed in the area of the thread on the housing section if they are to remain impermeable to liquid. If the pass-through openings are formed in another location of the housing section and are to remain impermeable to liquid, the pass-through openings must be rendered watertight following insertion of the drive unit in the housing section or must have already been made watertight during the manufacture of the housing section.

SUMMARY

According to one aspect, a battery-operated toothbrush includes a drive unit, a housing defining an accommodation chamber configured to receive the drive unit, and a thermoplastic elastomer seal disposed on an outer surface of the housing. The housing includes a front end configured to receive a toothbrush head, an open end, opposite the front end, that provides access to the accommodation chamber, and a pass-through aperture, which extends from an outer surface of the housing to the accommodation chamber. The drive unit includes an engagement element configured to engage the pass-through aperture to retain the drive unit in the accommodation chamber. The thermoplastic elastomer seal extends into the pass-through aperture. A potion of the thermoplastic elastomer seal is elastically displaced by the engagement element when the engagement element engages the aperture.

In some embodiments, the engagement element includes spring-loaded elements. The spring-loaded elements can force the thermoplastic elastomer within the aperture outwardly, allowing the elements to engage a surface defining the aperture. This arrangement can help to hold the drive unit in the accommodation chamber of the housing section.

In certain embodiments, the engagement element engages so minimally in the pass-through aperture that the thermoplastic elastomer displaced by the engagement element does not significantly or visibly protrude at the outer surface.

In some embodiments, the toothbrush can advantageously provide a simple locking mechanism for engagement of the drive unit with the housing in such a way that substantially no moisture is able to penetrate the interior via the pass-through aperture because the aperture is sealed in a substantially watertight manner by the thermoplastic elastomer.

It would also be possible to apply blind holes to the inner wall of the bore of the housing section, in which the engaging elements formed thereon might then engage in locking manner when the drive unit is inserted. In order to achieve this, slides could be formed in the tool to make the blind holes from the inside during the manufacture of the plastic housing section. This however would generally require a more expensive injection molding tool.

In some embodiments, thermoplastic elastomers are formed as inserts to provide better grip and/or a more attractive design. In such embodiments, a locking mechanism such as is described above is practical, without increasing production or assembly costs. Such thermoplastic surface elements may also be contrasted with the housing in terms of color, so that they may also lend a distinctive character to the design of the housing in addition to providing better grip.

In certain embodiments, a recessed region is provided adjacent the pass-through aperture on the outer surface of the housing, and like the pass-through aperture, the recessed region is also covered by the thermoplastic elastomer. In this way, the surface of the housing may also be altered by formed elastomer surface elements.

In some embodiments, the engagement element can include a latch member sufficient to ensure a secure hold after the engagement element is engaged in the pass-through aperture. In certain cases it may be possible to release the engagement element from the pass-through aperture and thus remove the drive unit from the accommodation chamber of the housing by pressing the thermoplastic elastomer radially inward from the outside in the area of the pass-through aperture such that the engagement element is moved radially inward until a frontal face of the engagement element no longer overlaps the pass-through aperture. Generally, however, the drive unit is fixed in the accommodation chamber of the housing, so that it may no longer be removed by the consumer after its assembly.

In some cases, a particularly secure connection between the drive unit and the housing section can be achieved where a wall of the pass-though aperture and a support surface of the engagement element extend substantially perpendicularly to the direction of movement during assembly of the drive unit in the accommodation chamber of the housing.

According to another aspect, a method for manufacturing a battery operated toothbrush includes molding a housing defining an accommodation chamber configured to receive a drive unit assembly. The housing includes a first end configured to receive a toothbrush head; an open end, opposite the first end, providing access to the accommodation chamber for installation and removal of the drive unit assembly; and a pass through aperture extending from an outer surface of the housing to the accommodation chamber. The method also includes molding a thermoplastic elastomer seal on the outer surface of the housing, the seal extending into the pass-though aperture; and disposing a drive unit assembly in the accommodation chamber, the drive unit assembly including an engagement element adapted to engage the pass through aperture when the drive unit assembly is disposed in the accommodation chamber, wherein a portion of the thermoplastic elastomer seal is elastically displaced by the engagement element when the engagement element engages the aperture.

Thus, after the pass-through aperture is formed in the housing, a thermoplastic elastomer seal can be molded over the pass-through aperture 35 using a second molding process. A spring-loaded engagement element acting radially outwardly can be disposed either on the drive unit itself or on the retaining element connected to the drive unit, and can be configured to engage the pass-through aperture sealed by thermoplastic elastomer when the drive unit is inserted in the housing and aligned with the aperture. The outwardly acting spring force of the engagement element can be of such a magnitude that it slightly forces the thermoplastic elastomer radially outward at least far enough to allow it to engage the pass-through aperture, thereby ensuring a secure hold or fixture of the drive unit in the accommodation chamber of the housing.

In certain embodiments, the engagement element can engage the pass-though aperture so minimally that the thermoplastic elastomer displaced by the engagement element does not significantly or visibly protrude at the surface, which would ultimately result in an elevation or bulge.

DESCRIPTION OF DRAWINGS

FIG. 1 is a cross-sectional view of an embodiment of a battery-operated toothbrush showing a drive unit inserted in an accommodation chamber defined by a housing.

FIG. 2 is a detailed view showing an engagement element of the drive unit engaging a pass-though aperture of the housing of the toothbrush of FIG. 1.

DETAILED DESCRIPTION

FIG. 1 shows a battery-operated toothbrush including a housing 2 having a first end 3 with a neck section 5 furnished with a toothbrush head 4 shown attached by clips. Neck section 5 and toothbrush head 4 with bristles 6 formed thereon are represented by dashed lines. An accommodation chamber 44 is formed in blind hole 7 of housing 2. An elongated retaining element 8 is shown located in front section 46 of accommodation chamber 44. The retaining element 8 supports electric drive motor 9, rocker switch 10, electrical wires 11, 12, and contact terminals 14, 15 extending from a battery 13 (shown with dashed line). A drive shaft 16 protrudes from drive motor 9 forward to first end 3, and an eccentric mass 17 is attached to drive shaft 16.

Housing 2 includes two apertures 18, 19 arranged one behind the other at the level of rocker switch 10. Apertures 18, 19 are sealed by elastomer walls 20, 21. Elevations 22, 23 on walls 20, 21 protrude outward and serve as actuating mechanisms for rocker switch 10. When an elevation 22 or 23 is actuated, the elastomer wall 20 or 21 is pushed inward to the point that either a left end 24 or a right end 25 of rocker switch is pivoted slightly about a pivot point 26 of rocker switch 10. If a loss of power occurs, causing the device 1 to be switched off, an angle element 27 formed on the right end 25 of rocker switch 10 engages between one of battery poles 28 (i.e., the negative pole or the positive pole) and contact terminal 15, so that no power may flow across electrical wires 11, 12 to drive motor 9, causing drive motor 9 to be switched off.

Battery 13 protrudes partially from open end 29 formed on the end of housing 2 and is retained in bore 7 by spring action produced at the free end of contact terminal 14. To seal opening 29, an end 30 of housing 2 is furnished with a thread 31. A protective cap 32 with a correspondingly formed thread (not shown) is screwed onto the end 30 in such a way that protective cap 32 (shown with dashed lines) seals opening 29 impermeably. At the same time, an O-ring 33 engages the inner surface of protective cap 32 and thus produces a leak-proof connection between protective cap 32 and threaded section 34.

As shown in FIG. 1, a pass-through aperture 35 is formed in housing 2. Pass-through aperture extends radially through the wall of housing 2 and is sealed by thermoplastic elastomer mass. A laminar-formed channel 36 connects with pass-through aperture 35 and extends over part of the perimeter of housing section 2. Channel 36 is also sealed by a thin film 47 of thermoplastic elastomer, which is structured on its surface 45 with transverse striations 37. Surface 45 of thermoplastic elastomer material 39 forms a portion of outer surface 50 of toothbrush 1, which includes a polypropylene generated surface 49.

As illustrated in FIG. 2, an engagement element 38 (e.g., a latch member) is disposed on retaining element 8. In some embodiments, the toothbrush includes two engagement elements arranged circumferentially adjacent one another. When retaining element 8 is connected to drive unit 9 and inserted in direction X, latch member 38 engages pass-though aperture 35. At the same time, the elastomer material 39 that is located in pass-though aperture 35 is displaced outwardly until a frontal surface 40 of latch member 38 lies substantially flush with wall 41. When retaining element 8 is inserted in bore hole 7 in direction X, tip 42 formed at the front of latch member 38 slides along wall 43 of bore hole 7 until it reaches pass-through aperture 35, at which time tip 42 engages pass-through aperture 35 because of its pre-biased position, and displaces thermoplastic material 39. Housing 2 can be injection molded from a relatively hard plastic material (e.g., polypropylene) onto or on which thermoplastic elastomer 39 can be injection molded in a second extrusion tool. The softer thermoplastic elastomer is indicated in FIGS. 1 and 2 by cross hatching 48.

What is claimed is:
1. A battery-operated toothbrush, comprising:
 a drive unit;
 a housing defining an accommodation chamber configured to receive the drive unit, the housing comprising
 a front end configured to receive a toothbrush head, an open end, opposite the front end, providing access to the accommodation chamber for installation and removal of the drive unit, and a first surface extending from an outer surface of the housing to the accommodation chamber and defining a pass-through aperture; and a thermoplastic elastomer seal disposed on the outer surface of the housing and extending over the pass-through aperture, wherein the drive unit includes an engagement element extending into the pass-through aperture and in engagement with the first surface of the housing, thereby retaining the drive unit in the accommodation chamber.

2. The battery-operated toothbrush according to claim 1, wherein the outer surface of the housing defines a recessed region disposed adjacent the pass-though aperture and sealed by the thermoplastic elastomer forming a graspable handle of the toothbrush.

3. The battery-operated toothbrush according to claim 1, wherein the engagement element comprises a latch member.

4. The battery-operated toothbrush according to claim 3, wherein a surface of the engagement element extends substantially transversely to a longitudinal axis of the toothbrush, the surface of the engagement element configured to engage the first surface of the housing.

5. The battery-operated toothbrush according to claim 4, wherein the first surface of the housing extends substantially transversely to the longitudinal axis of the toothbrush.

6. The battery-operated toothbrush according to claim 1, wherein the engagement element extends radially outward from a longitudinal axis of the housing during assembly of the drive unit in the accommodation chamber.

7. The battery-operated toothbrush according to claim 1, wherein the engagement clement comprises a spring-loaded member.

8. The battery-operated toothbrush according to claim 1, wherein the thermoplastic elastomer seal provides a substantially fluid tight seal.

9. The battery-operated toothbrush according to claim 1, wherein the housing further comprises a threaded section proximal to the open end and configured to receive a sealing cap having a corresponding thread.

10. The battery-operated toothbrush according to claim 9, wherein the pass-through aperture is longitudinally spaced apart from the screw thread.

11. The battery-operated toothbrush according to claim 1, wherein the housing is injection-molded.

12. The battery-operated toothbrush according to claim 11, wherein the thermoplastic elastomer seal is injection molded onto the outer surface of the housing.

13. The battery-operated toothbrush according to claim 1, wherein a portion of the thermoplastic elastomer seal extends into the aperture.

14. The battery-operated toothbrush according to claim 13, wherein the portion of the thermoplastic elastomer seal extending into the aperture is displaced by the engagement element at least far enough to allow the engagement element to engage a surface defining the aperture when the drive unit is disposed in the chamber.

15. The battery-operated toothbrush according to claim 14, wherein the displacement of the seal does not cause visible protrusion of the seal at an outer surface of the thermoplastic elastomer.

* * * * *

UNITED STATES PATENT AND TRADEMARK OFFICE
CERTIFICATE OF CORRECTION

PATENT NO. : 7,401,377 B2  Page 1 of 1
APPLICATION NO. : 11/292401
DATED : July 22, 2008
INVENTOR(S) : Andreas Birk It is certified that error appears in the above-identified patent and that said Letters Patent is hereby corrected as shown below:

Title Page Item [56]
Column 1, Foreign Application Priority Data:
Delete "10 2004 057 566" and Insert --10 2004 057 566.5--

Column 5, Claim 2, Line 15:
Delete "pass-though" and Insert --pass-through--

Column 6, Claim 7, Line 2:
Delete "clement" and Insert --element--

Signed and Sealed this

Fourth Day of November, 2008

JON W. DUDAS
*Director of the United States Patent and Trademark Office*